United States Patent
Kuznetsov et al.

(10) Patent No.: US 9,329,138 B2
(45) Date of Patent: May 3, 2016

(54) METHOD FOR STANDOFF DETECTION AND ANALYSIS OF OBJECTS

(71) Applicant: Apstec Systems USA LLC, Owings Mills, MD (US)

(72) Inventors: Andrey Kuznetsov, St. Petersburg (RU); Valery Averyanov, St. Petersburg (RU); Stanislav Vorobyev, St. Petersburg (RU); Igor Gorshkov, St. Petersburg (RU)

(73) Assignee: APSTEC SYSTEMS USA LLC, Owings Mills, MD (US)

( * ) Notice: Subject to any disclaimer, the term of this patent is extended or adjusted under 35 U.S.C. 154(b) by 0 days.

(21) Appl. No.: 14/426,239

(22) PCT Filed: Nov. 17, 2014

(86) PCT No.: PCT/US2014/065883
§ 371 (c)(1),
(2) Date: Mar. 5, 2015

(87) PCT Pub. No.: WO2015/077169
PCT Pub. Date: May 28, 2015

(65) Prior Publication Data
US 2016/0047757 A1  Feb. 18, 2016

Related U.S. Application Data

(63) Continuation-in-part of application No. 14/160,895, filed on Jan. 22, 2014, and a continuation-in-part of application No. 14/259,603, filed on Apr. 23, 2014, and a continuation-in-part of application No. 14/319,222, filed on Jun. 30, 2014.

(60) Provisional application No. 61/905,940, filed on Nov. 19, 2013, provisional application No. 61/945,921, filed on Feb. 28, 2014.

(51) Int. Cl.
*G01N 22/00* (2006.01)
*G01N 33/22* (2006.01)

(52) U.S. Cl.
CPC .............. *G01N 22/00* (2013.01); *G01N 33/227* (2013.01)

(58) Field of Classification Search
CPC ............................ G01N 22/00; G01N 33/227
See application file for complete search history.

(56) References Cited

U.S. PATENT DOCUMENTS

| | | | |
|---|---|---|---|
| 5,774,631 A * | 6/1998 | Chiabrera | G06N 3/0675 706/15 |
| 7,684,846 B2 | 3/2010 | Johnson et al. | |
| 2009/0119040 A1 * | 5/2009 | Zhdanov | A61B 5/417 702/65 |

(Continued)

FOREIGN PATENT DOCUMENTS

| | | |
|---|---|---|
| EP | 2505995 A1 | 10/2012 |
| GB | 2458465 A | 9/2009 |

*Primary Examiner* — Patrick Assouad
*Assistant Examiner* — Haidong Zhang
(74) *Attorney, Agent, or Firm* — Nadya Reingand (57) ABSTRACT

A method for standoff detection and analysis of objects comprises sending a signal through an inspection area, from a transmitter to a receiver, wherein the signal travels through objects in its path. If the signal encounters an object, through which it must travel, the speed of signal distribution decreases and its amplitude drops. A processor then determines the amplitude of the signal and whether the amplitude is above a given threshold, and if the threshold is met, further determining the shift in length of the signal's optical path, determining the thickness of the object, calculating the dielectric permittivity constant, and comparing this constant to known values of different materials to determine a preselected group of materials, to which the object in the inspection area belongs, and whether the inspected object belongs to a preselected group of dangerous objects. A system for detecting and analyzing such materials is also disclosed.

14 Claims, 7 Drawing Sheets

(56) References Cited

U.S. PATENT DOCUMENTS

| | | | | |
|---|---|---|---|---|
| 2011/0304698 A1* | 12/2011 | Andrey | ............... | G01S 13/887 348/47 |
| 2013/0022237 A1 | 1/2013 | Kuznetsov et al. | | |
| 2013/0033574 A1 | 2/2013 | Kuznetsov et al. | | |
| 2014/0070111 A1* | 3/2014 | Rappaport | ........... | G01N 23/083 250/395 |

\* cited by examiner

METHOD FOR STANDOFF DETECTION AND ANALYSIS OF OBJECTS

CROSS-REFERENCE TO RELATED APPLICATIONS

This patent application is a National Stage application from PCT application No. PCT/US14/65883 filed on Nov. 17, 2014. This patent application claims priority to, and incorporates fully by reference, U.S. patent application Ser. No. 14/319,222 "METHOD FOR STANDOFF DETECTION AND ANALYSIS OF OBJECTS", filed on Jun. 30, 2014, which claims priority to U.S. Provisional Patent Application No. 61/905,940, filed Nov. 19, 2013; it also claims priority to C-I-P U.S. Ser. No. 14/160,895 "ACTIVE MICROWAVE DEVICE AND DETECTION METHOD" filed on Jan. 22, 2014; it also claims priority to U.S. patent application Ser. No. 14/259,603 "SMART SCREENING BARRIER AND SYSTEM", filed on Apr. 23, 2014, which claims priority to U.S. provisional patent application No. 61/945,921, filed on Feb. 28, 2014.

FTFLD OF THE INVENTION

This invention relates to methods for standoff detection of objects and measurement of the dielectric characteristics of such objects in real time. In particular, it relates to methods for detection of explosives hidden on the human body, in hand luggage, and in backpacks.

BACKGROUND OF THE INVENTION

The detection of so-called "suicide bombers", who carry bombs on their body and activate them immediately at the slightest sign of a security response, continues to be a largely important security issue today.

At present, metal detectors are used, as well as various types of gas trace detectors, X-ray machines and specially-trained dogs. Currently, developed detection approaches in various countries include detectors that are based on the following principles: NQR effect, Raman backscattering, dielectric portals, passive and active devices for human body inspection (terahertz frequencies), passive radars (millimeter frequencies) and active microwave portals.

Modern inspection methods and devices continue to lack important features: they don't provide standoff covert inspection (i.e., they cannot detect a "suicide bomber" in real time or perform counteractions against him before he activates an explosive); they cannot automatically determine the danger/risk level of the detected object and have a very high false alarm rate, which limits use in real conditions, e.g., in a moving crowd.

The prior art, in general, lacks at least half of the following features: Standoff inspection; automatic inspection; real time inspection; covert inspection; environmental independence; safety for human health; possibility to associate an alarm signal with a certain person; mobility; and relatively low cost.

The present invention provides for a method for standoff detection of objects based on measuring a thickness of said object and further calculating a dielectric permittivity value; comparing said dielectric permittivity value to a database of reference dielectric permittivity values, so as to determine to which preselected group of objects the object belongs and whether the object belongs to a preselected group of dangerous objects. Goods stolen from a supermarket can e.g. form a preselected group of objects. A preselected group of dangerous objects could in particular be formed by a group of explosive materials or a group of improvised explosive devices (IED).

A variety of methods exist for measuring a complex dielectric permittivity value of solid materials using high frequency techniques. Methods employing microwave frequency ranges are based on electromagnetic wave propagation in a medium or wave processes on the borders of two media. All known methods are based on registration of the phase change when the microwave passes through the dielectric object. These methods operate by linking the phase change value to the value of the dielectric permittivity of the target material. These connections can vary in each particular case, thus explaining the variety of measurement methods used to determine a material's complex dielectric constant ($\in = \in' + \in''$) and dissipation factor ($\tan(\delta) = \in''/\in'$), wherein $\in'$ and $\in''$ are the real and imaginary parts of the dielectric constant, respectively.

Several methods exist for measuring the dielectric constant of material based on the analysis of a signal at high or super-high frequencies:

(1) Methods which use directional waves: waveguide methods with coaxial line and rectangular waveguides; using one of the most common waveguide methods—the short-circuit method—one determines characteristics of a dielectric sample located at the shorter end of the waveguide according to the phase and coefficient of a wave moving along the line.

(2) Resonant methods, which measure resonance frequencies and quality factors.

(3) Methods which use waves in free space, e.g., based on measuring the coefficients of reflection and transmission, i.e., quasi-optic methods used to measure parameters in free space.

The choice of a method to be used is determined by the type of measurements (laboratory researches, industrial nondestructive control, etc.), frequency range, and a material's characteristics. The main disadvantage of the second and third methods above (2, 3) is their incompatibility with odd or abnormally shaped objects. Such methods are capable of producing measured samples of materials having two plane surfaces (e.g., rectangular). Due to the variety of shapes of dangerous dielectric objects today, existing methods must be improved to carry out standoff inspection of a monitored space and determine the dielectric characteristics of all objects, including those that are irregularly-shaped.

Additionally, methods using directional waves (1, above) and resonant methods (2, above) are the most accurate methods in the decimeter and centimeter wave range; however, they require using a samples fitting waveguide or a resonator line cross-section.

The closest prior art to the proposed method is a method to measure a dielectric constant described in RF Patent No. 2418269, "Method and device for tomographic measurements of multi-phase flow." This disclosed method is based on the irradiation of a dielectric multi-phase liquid medium (gas-liquid mixture), located inside a Venturi tube, with microwave electromagnetic radiation, further comprising recording and analysis of the transmitted field. The complex dielectric constant is determined by measuring the phase constant and the attenuation rate of a plane electromagnetic wave propagating inside the Venturi tube. The method comprises measuring the difference between phases of electromagnetic waves for two receiving antennas, placed within the tube at different distances from a third, transmitting antenna. The phase is measured at two or more frequencies, within the range of 1 MHz and 10 GHz. The attenuation rate is measured similar to the phase constant of the propagating wave, except that, instead of phase difference, the dissipation difference, $k=\alpha+i\beta$ (where k=complex propagation constant, $\alpha$=attenuation rate, and $\beta$=phase constant of the wave) is estimated.

The disadvantages of the above method include the following: (1) the requirement to use at least 3 antennas (1 transmitting and 2 receiving antennas); (2) the requirement to use a dielectric liquid in a special Venturi tube, thus not allowing for measurements of solid objects or covert standoff inspection and detection; (3) the receiving antenna is located close to the transmitting antenna, thus the model of plane wave propagation must be corrected considering (a) dependence between the distance between receiving antennas and the length of the wave received by them, and (b) the weak dependence between this distance and the conductivity of the required multi-phase liquid medium (additional dependencies into the algorithm makes required calculations more complex and time-consuming); (4) the method is only useful under laboratory conditions (e.g., detection of planar/simple objects).

SUMMARY OF THE INVENTION

Disclosed herein is a method for detecting and analyzing an object in a monitored area comprising emitting an electromagnetic/microwave (EM/MW) signal via one transmitter through the monitored area, the signal travelling through the monitored area and through any object along its path towards one receiver located at a distance opposite of said one transmitter, the receiver detecting an amplitude and a phase (complex amplitude) of a received EM/MW signal, the receiver further performing a first processing of the signal to determine whether said amplitude is above a preset amplitude threshold, and further performing a second processing of the signal if the preset amplitude threshold is met. The second processing comprises determining a shift in a length of an optical path of said EM/MW signal, compared to an optical path of the same signal through free space, wherein the shift occurs due to the signal transmitting through an object. This data regarding the shift is then sent to a processor. Also measured is the thickness (t) of said object, using any known or disclosed methods, which is also sent to said processor. The thickness (t) of the object is measured in direction of a straight line between said transmitter and said receiver. The processor further calculates a dielectric permittivity value ($\in$) of said object via a relationship of said shift equating to ($t*(\sqrt{\in}-1)$), and the processor compares the object's dielectric permittivity value to a database of reference dielectric permittivity values, in order to determine to which preselected group of objects the said object belongs and whether the object belongs to a preselected group of dangerous objects.

In some aspects, the shift in the length of the optical path is calculated by a Fourier transform of the relation between a signal's complex amplitudes in the presence of the object within the inspected area of space and the signal's complex amplitudes in the absence of the object within the inspected area of space.

In some aspects, many space distributed EM/MW signals may be combined to form a real time distribution map of dielectric permittivity value data.

In some aspects, the method further comprises sending a confirmation or alarm signal in the presence of an object belonging to a particular preselected group of dangerous or non-dangerous objects. In some aspects, the signal is a silent signal, such as an optical signal or a vibrational signal. A silent signal can be any signal that is not notable by an individual carrying or hiding an object of a preselected group of objects.

In some aspects, the method further comprises using one or more additional transmitters transmitting an EM/MW signal to said receiver. In some aspects, the method further comprises using one or more additional receivers receiving an EM/MW signal from one or more transmitters. In some aspects, one transmitter comprises an array of transmitting antennas. In some aspects, one receiver comprises an array of receiving antennas. In some aspects, one transmitter comprises an array of transmitting antennas and one receiver comprises an array of receiving antennas. In some aspects, each one transmitter corresponds to only one receiver and each receiver corresponds to only one transmitter.

In some aspects, the method is capable of detecting an object of an irregular shape. In some aspects, the method detects objects of regular shapes.

In some aspects, the object is detected in space and in time as it moves through the monitored area.

In some aspects, the object is optically transparent media. In some aspects, the object is optically non-transparent media.

A system for detecting objects in a monitored space, according to the methods described herein, is also disclosed.

BRIEF DESCRIPTION OF THE DRAWINGS

FIG. 4 shows an example of how a distribution map is created by the method described herein.

DETAILED DESCRIPTION OF THE PREFERRED EMBODIMENT

The present invention significantly enlarges application of the methods described above, particularly by detecting and locating objects of all types of shapes in space at a distance (i.e., standoff detection) and measuring a material's dielectric constant automatically and classifying objects in preselected group and in real time.

The method to determine the dielectric constant of a material comprises analysis of the amplitude and phase of a transmitted broadband quasi-coherent microwave radiation (the preferred frequency range is 8-18 GHz), which is transmitted through a monitored space. Advantages of the present invention include: (1) creation of a "dielectric permittivity map" of a space being monitored and, after automatic analysis, determination of a corresponding domain (i.e. a stored material value) with the same dielectric permittivity constant; (2) recording changes in the "dielectric permittivity map" in real time to measure the dielectric constant of a moving target (not only for detection, but also for surveillance of moving dielectric targets); (3) recording distribution of a dielectric constant (i) in space and (ii) in time; (4) determination of the dielectric constant of an object of irregular shape (i.e. any shape); (5) determination of the dielectric constant of optically transparent and non-transparent media.

According to the method described herein, inspection of an object located within a monitored area is based on analyzing the parameters of quasi-coherent microwave radiation transmitted through the monitored area. Such analysis allows for the dielectric constant, shape, and volume of an object carried on the body or in luggage to be determined.

The present method of determining the dielectric constant of an object is based on the effect of the lengthening of an optical path of electromagnetic radiation when it goes through a dielectric object. For example, if a dielectric object with a thickness (t) and a dielectric constant ($\in$), is placed between a receiver and a transmitter, wherein the receiver and transmitter are placed at a distance (L) from each other, the optical path will be equal to $(L+t*(\sqrt{\in}-1))$. One method to determine the lengthening of an optical path of electromagnetic radiation is the Fourier transformation, applying the values corresponding to the change of phase and amplitude of electromagnetic radiation through a field with a dielectric object in it, compared with the phase and amplitude for the same field with no objects in it (i.e. "free space").

In one embodiment, the Fourier transformation modulus is expressed by the following formula:

$$AF(dist) = \left[\sum_{j=1}^{N_f} A_{otnj} \cdot \cos\left(Phase_{otnj} + Freq_j \cdot \frac{dist \cdot 2\pi}{c}\right)\right]^2 +$$

$$\left[\sum_{j=1}^{N_f} A_{otnj} \cdot \sin\left(Phase_{otnj} + Freq_j \cdot \frac{dist \cdot 2\pi}{c}\right)\right]^2$$

The working equation above comprises the following variables:

$$A_{otnj} = \frac{Amp_j}{Ampfree_j} = \text{relative amplitude, } j = \text{frequency number,}$$

where $Amp_j$=amplitude of the received signal for the j-frequency transmitted through the inspected volume, j=frequency number; and where $Ampfree_j$=amplitude in free space (i.e., no objects between receiver and transmitter), j=frequency number;

$$Phase_{otnj} = \frac{(Phasefree_j - Phase_j) \cdot \pi}{180} = \text{relative phase for } i\text{-transmitter,}$$

$j$ frequency number, where
  $Phase_j$=operating signal phase for the signal transmitted through the inspected volume, j=frequency number; and where
  $Phasefree_j$=phase in free space, j=frequency number;
  $Freq_j$=frequency value; j=frequency number;
  $N_f$=quantity of frequencies used; and
  c=speed of light in vacuum.

The shift in a length of an optical path can be calculated from the AF(dist) distribution and equals the variable "dist" where the AF(dist) value is at its maximum. AF is an amplitude of the Fourier transform function. "dist" is the variable of AF(dist) distribution and can be considered as (axis "X" shifted at value L (optical length of free space)) in FIGS. 1-3. In case of "free space" the shift in a length of an optical path is zero and the AF(dist) value has its maximum at dist=0.

The method of the present invention comprises a method for detecting and analyzing an object in a monitored area, comprising: first emitting an electromagnetic/microwave (EM/MW) signal via one transmitter through the monitored area, thus transmitting said EM/MW signal through the monitored area, said signal transmitting through any object along a path directed towards one receiver located at a distance opposite of said one transmitter for receiving said signal, said receiver detecting an amplitude and a phase (i.e. complex amplitude) of a received EM/MW signal transmitted through the monitored area, said receiver further performing a first processing of said received signal to determine whether said amplitude is above a preset amplitude threshold, said receiver further performing a second processing of said received signal if said preset amplitude threshold is met, said second processing comprising determining a shift in a length of an optical path of said EM/MW signal, compared to an optical path of the same signal through free space, said shift occurring due to said EM/MW signal transmitting through object, sending data regarding said shift to a processor, then measuring a thickness of said object (designated as t) using any method according to the present invention or known in the art (e.g., using a set of video cameras positioned to view the space of the monitored area), and sending data regarding said thickness to said processor, wherein said processor further calculates a dielectric permittivity value ($\in$) of said object via a relationship of said shift equating to $(t*(\sqrt{\in}-1))$, and said processor comparing said dielectric permittivity value to a database of reference dielectric permittivity values (this database forms preselected groups of objects which are deemed dangerous or non-dangerous, for example), in order to determine which preselected group of objects the monitored object belongs to and whether the object belongs to a preselected group of dangerous objects (i.e. is a dangerous object, e.g., because of a high dielectric permittivity value).

In some aspects, the shift in the length of the optical path may be calculated by a Fourier transform of the relation between a signal's complex amplitudes in the presence versus the absence of the object (the same signal going through free space) in the controlled/inspected area of space.

Figure 1:
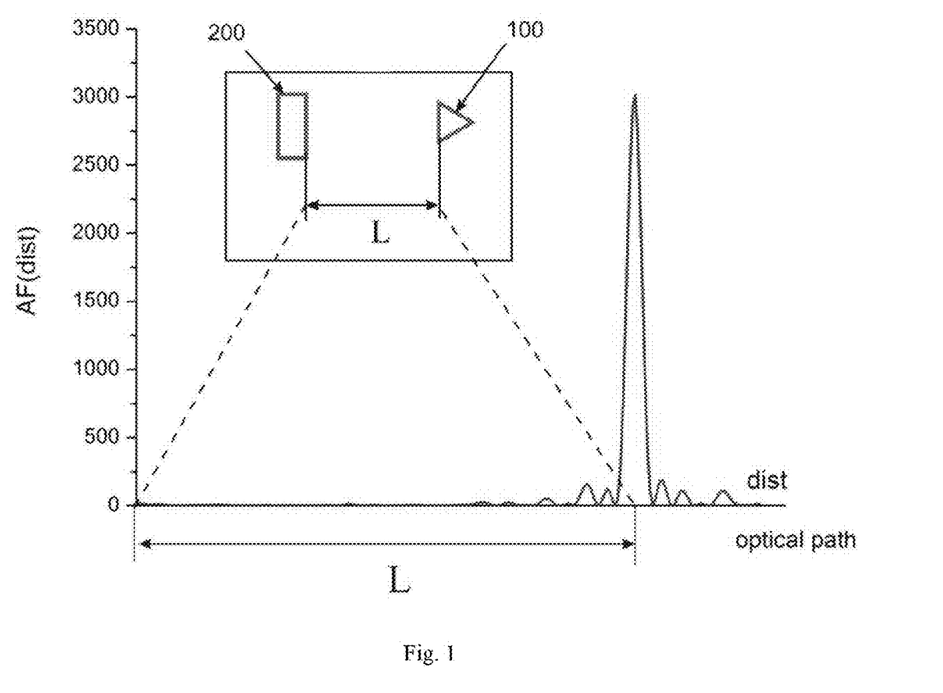
FIG. 1 shows an example of "free space" Fourier transform data.
Figure 2:
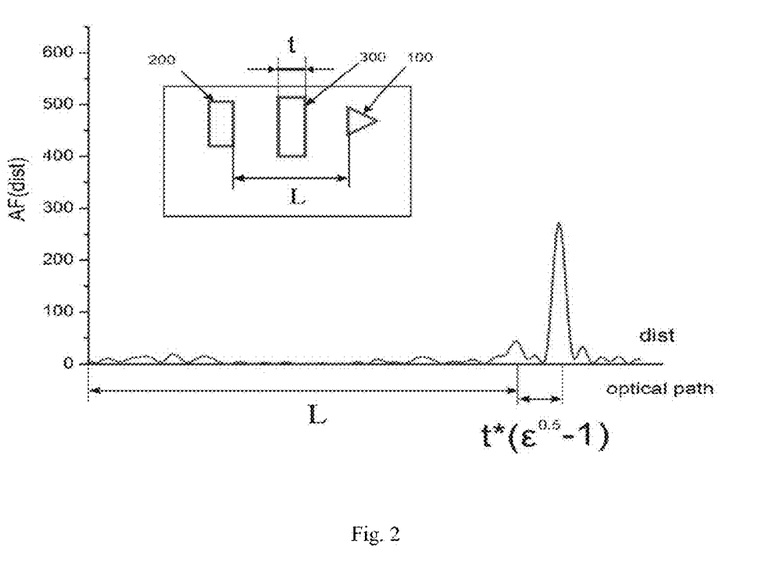
FIG. 2 shows an example of Fourier transform data when there is a dielectric between a receiver and transmitter.
Figure 3:
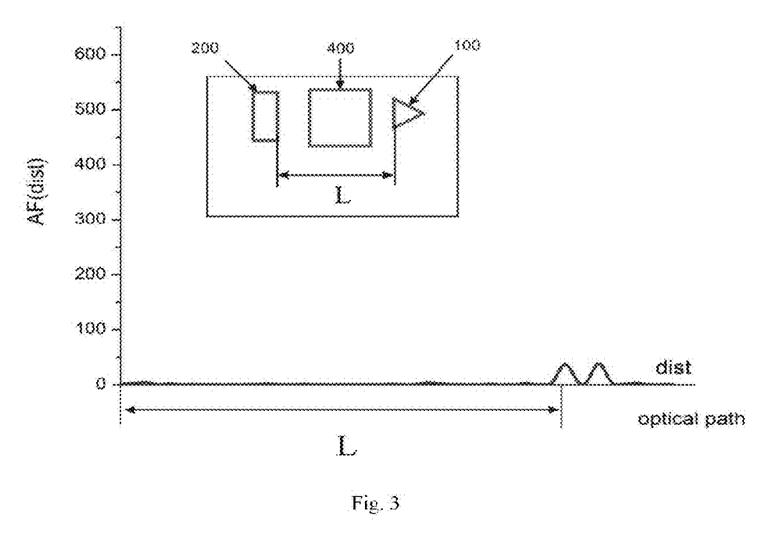
FIG. 3 shows an example of Fourier transform data when there is a conductor between a receiver and transmitter.

FIGS. 1, 2, and 3 show an example of the type of experimental data (frequency range 8-18 GHz) obtained by the Fourier transform method for free space (i.e., no object in the field between a transmitter 200 and a receiver 100) (FIG. 1), a dielectric object 300 located between a transmitter 200 and a receiver 100 (FIG. 2), and a conducting object (i.e. conductor) 400 located between a transmitter 200 and a receiver 100 (FIG. 3). As shown in FIGS. 2 and 3, a dielectric placed between the receiver and the transmitter causes a shift of the Fourier transform maximum at a distance related to the dielectric object's thickness (t) and its dielectric constant value ($\in$) the relationship and shift being equal to the value, $t*(\in^{0.5}-1)$. The amplitude of the function is also less than the amplitude measured in "free space" due to scattering and absorption in the dielectric object. Thus, by setting certain parameters for searching—a range of maximum shift and a range of corresponding amplitudes—it is determined whether a dielectric object is present or not present.

As shown in FIG. 3, when there is a conductor between receiver and transmitter (e.g., a human body), the amplitude of the Fourier transform maximums is tens of times lower than that through free space. Thus, by setting an amplitude threshold, it is determined whether objects of a specific material are located in the monitored field. The preset amplitude threshold values also help to distinguish conductors from dielectrics.

The presently claimed method is also capable of creating a "space map" (or "distribution map") of dielectric permittivity value distribution. Due to the existence of an array of transmitting (or receiving) antennas—for example, an antenna array comprising many smaller elementary transmitters—the Fourier transform is calculated separately for each such transmitter. Thus, a distribution of projections of dielectric constants for an interrogated object is built along the plane of an antenna array. By (1) reconstructing a distribution of the dielectric constant value of objects located in or moving through a monitored area and (2) distinguishing particular portions of that space where the dielectric constant values coincide to the dielectric constant values of real explosives or other dangerous objects, the method determines (1) if such objects exist and (2) where such objects exist. In general, any type of dielectric may be detected (not limited to explosives), depending on the sensitivity threshold, which can be present to any given value. The dielectric permittivity value of an object is determined by simultaneously measuring the phase and the amplitude of a microwave (MW) signal traveling through the monitored area and passing (i.e. transmitting) through a target moving through the area. A single source or multiple sources of MW radiation are used, and one receiver or multiple receivers of MW radiation are employed. In some embodiments, the source(s) of radiation generate(s) radiation at multiple frequencies.

A received signal (or signals) is (are) used to obtain information about changes in the length of an optical path. The microwave signal transmitted through an interrogated object such as, for example, a carried bag, is compared with a signal which travels the same distance without the bag in its way (i.e. the optical path's length in free space). In order to determine the change in the optical path length, the shift is measured between the maximal values of (1) the signal through the object (i.e. the converted signal, measureable using the Fourier transform formula above) and (2) the same signal when there is no object at all. Once the "shift" is measured, dielectric permittivity value may be determined from equation $$\sqrt{\varepsilon} = \frac{shift}{t} + 1,$$

where t is the thickness of the object, and $\in$ is the dielectric permittivity value. Value t can be measured by various different instruments and other known methods in the art (e.g., but not limited to, video systems to obtain a corresponding stereo image).

The recognition of objects as potentially dangerous or benign according to their dielectric properties is based on the fact that all explosives, e.g. TNT, RDX, tetryl, etc., have a real-number coefficient of their dielectric permittivity ranging between 2.8 and 7. Everyday items that are not dangerous, e.g. plastics and books, however, have a dielectric permittivity value of no more than 2.5. Thus, by setting detection thresholds based on this information, it is possible to detect when an object of abnormal dielectric permittivity enters and moves through the monitored area.

Figure 4A:
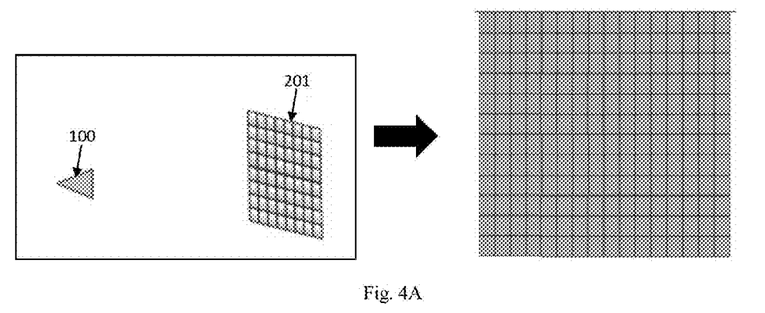
FIG. 4A shows a scenario and map corresponding to no objects in the inspection field (i.e., between a receiver and transmitter).
Figure 4B:
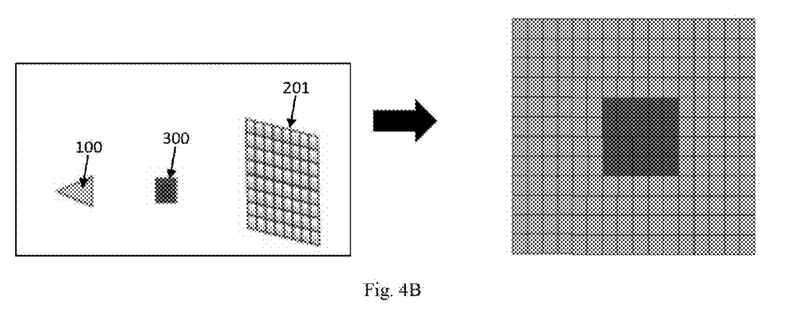
FIG. 4B shows a scenario and map corresponding to a dielectric object in the inspection field.
Figure 4C:
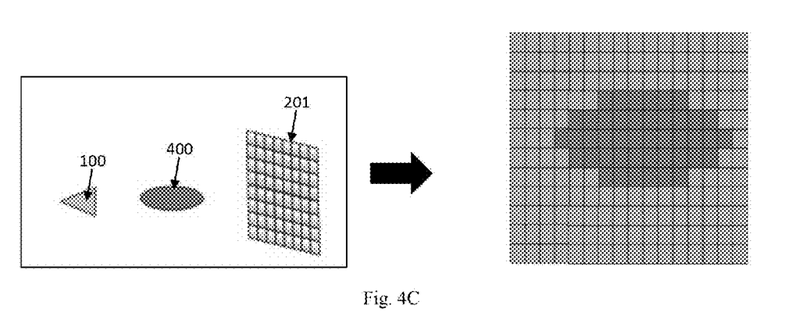
FIG. 4C shows a scenario and map corresponding to a conductor object in the inspection field.
Figure 4D:
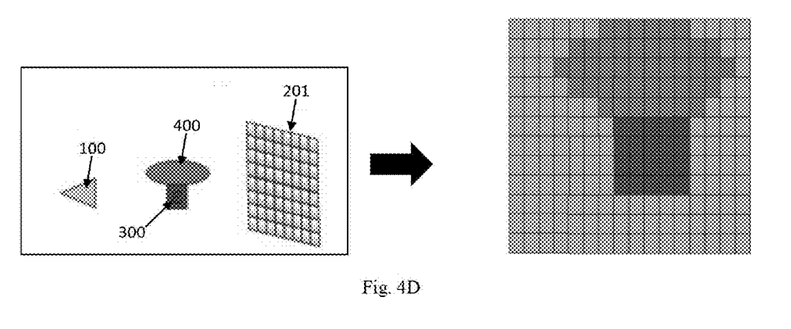
FIG. 4D shows a scenario and map corresponding to both a dielectric and a conductor in the inspection field.

FIG. 4 illustrates an example of a model distribution for situations where, between a transmitter array 201 and a receiver 100 (note that either a receiver or a transmitter can comprise an array, although this example shows only a transmitter array), there is free space (FIG. 4A), there is a dielectric 300 (FIG. 4B) there is a conductor 400 (FIG. 4C), or there is both a dielectric 300 and a conductor 400 (FIG. 4D). Thus, according to the distribution of Fourier transform functions for different individual transmitters in the antenna array (e.g., quantity, how close the similar responses are, etc.), it is determined whether there is a dielectric (or other) object within the inspected area. Also in inspection area, the size of an object can be determined as well (e.g., by means of stereo video systems).

In the preferred embodiment of the present invention, the physical dimensions of the inspected object are required to be detected. To obtain this information, various additional technologies are coupled with the microwave imaging (i.e. Fourier transform) method described herein video systems to obtain a corresponding stereo image). This combined method is integrated into various types of inspection systems used for detecting potentially dangerous objects on the human body (e.g., explosives). Together with the measurement of the optical path lengths geometric dimensions and shape of the inspected object are measured by constructing a 3D stereo optical image of the object using system of video cameras comprising a stereo video pair. Joint information about (1) dimensions of an object in a monitored area and (2) the value of the shift due to the lengthening of an optical path of electromagnetic waves of a chosen frequency range allows for the determination of the dielectric constant of the object. This value, together with measurements of geometric dimensions and shape analysis, is then used to determine the level of danger associated with the object by comparing in the object's characteristics with a database of reference characteristics of dangerous items including but not limited to explosive devices and explosive materials.

The proposed method can be used to determine the dielectric constant of different dielectric objects including but not limited to solids and liquids. One important condition under which the method operates is a low level of radiation absorption by the inspected object (this number preferably, and optimally, has a value of zero).

Figure 5A:
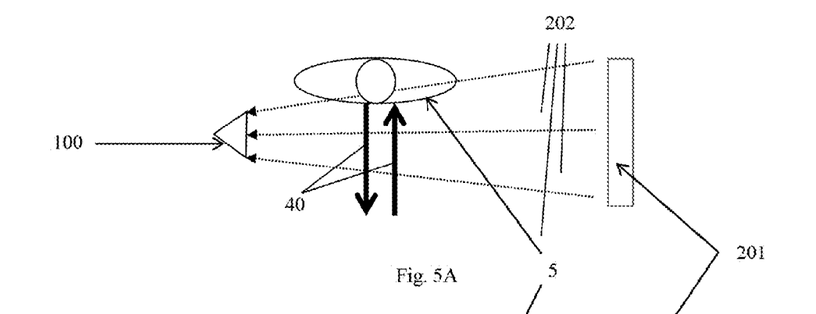
FIG. 5A shows an example of a configuration where one antenna array transmits signals and one receiving antenna receives the signals transmitted.
Figure 5B:
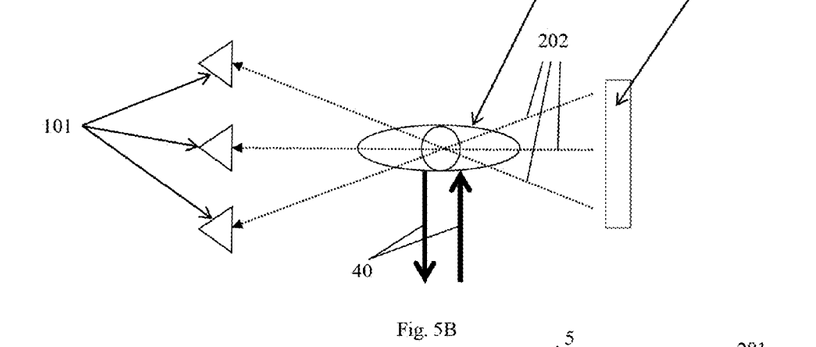
FIG. 5B shows an example of a configuration where one antenna array transmits signals and three receiving antennas receive the signals transmitted.
Figure 5C:
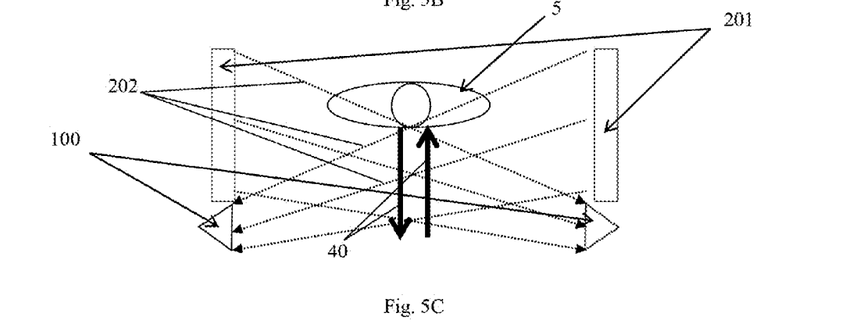
FIG. 5C shows an example of a configuration where one (transmitting) antenna array transmits signals and another (receiving) antenna array receives the signals.

FIGS. 5A-5C show examples of different configurations for the presently claimed method. A single transmitter 200 and a single receiver 100 can be employed, multiple transmitters 200 and/or receivers 100 can be employed, an array (or matrices) of transmitters 201 and/or an array (or matrices) of receivers 101 can be employed in various embodiments of the present invention. FIG. 5A specifically shows an array of transmitters (i.e. a transmitter array) 201 sending signals (e.g., electromagnetic, microwave, etc.) 202 to one receiver 100, the signal transmitting through any individual and carried or hidden items 5 as the individual and items move through the monitored area in either direction 40. FIG. 5B specifically shows a transmitting array 201 sending signals 202 to an array of receivers (i.e. a receiver array) 101, each signal transmitting through any individual and carried or hidden items 5 as the individual and items move through the monitored area in either direction 40. FIG. 5C specifically shows transmitter arrays 201 located on opposite sides of a monitored area sending signals 202 to individual corresponding receivers 100 located at a distance opposite their corresponding transmitter arrays. Each signal transmits through any individual and carried or hidden items 5 as the individual and items move through the monitored area in either direction 40.

Figure 6:
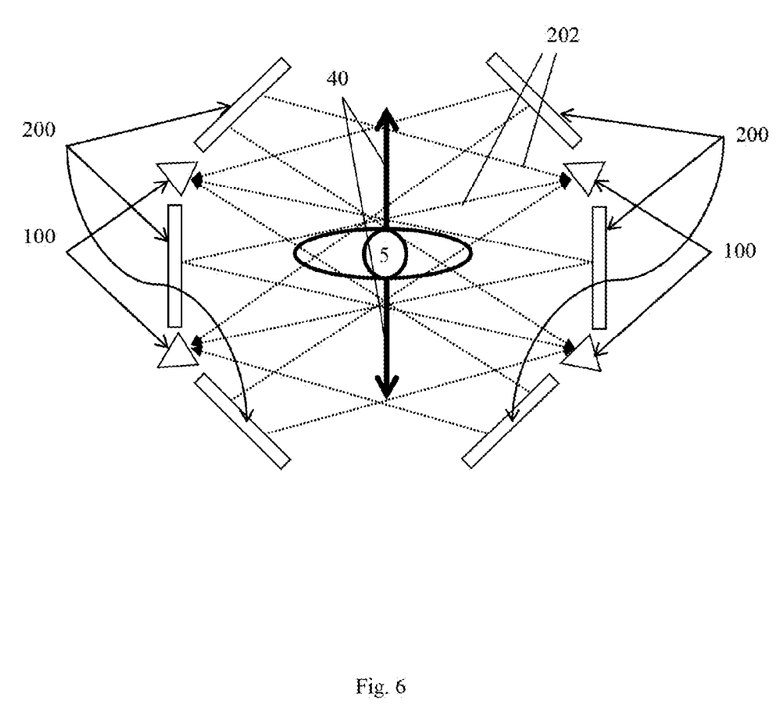
FIG. 6 shows an example of a configuration where several transmitting and receiving antennas are placed in a circular or spherical manner about a field of inspection.

FIG. 6 shows a different embodiment (in the form of another configuration) of the presently claimed method. In this embodiment, transmitters 200 and receivers 100 are positioned in a circular (360 degree) fashion about a field of inspection, allowing for collection of signal data from different angles relative to a target. Such a design is potentially further developed into a 3-dimensional configuration of transmitters and receivers (i.e., spherical placement) to include even more angles for data collection. The transmitters and receivers may replace each other and the essence of the invention will remain the same. Each signal transmits through any individual and carried or hidden items 5 as the individual and items move through the monitored area in either direction 40.

Figure 7:
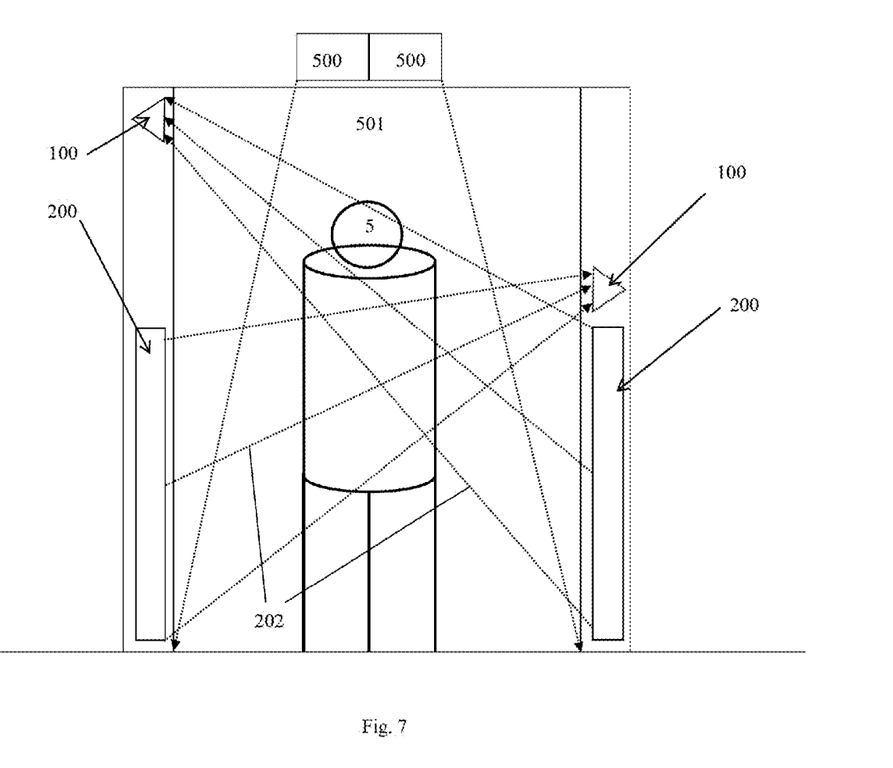
FIG. 7 shows an example of a configuration where two transmitting antenna arrays are placed opposite receiving antennas, and this MW-imaging mechanism is coupled with a video-imaging mechanism, to create a walk-through security portal for real-time inspection.

FIG. 7 details yet another embodiment and configuration of transmitters 200 and receivers 100. In this embodiment, the inspection field is located in a portal through which inspected targets continuously move. Inspection is performed in real time as a person moves through the portal. This particular configuration comprises two transmitter arrays 201 (each array comprises, for example, 512 elements, wherein each element transmits its own wave/signal) placed at different sides of a portal, and two receiving antennas 100 placed across from, or opposite, the transmitting antenna array 201 in a manner such that the inspection zone is made as large as possible (e.g. various angles for capturing different viewpoints based on such angles of wave propagation). The configuration of this particular embodiment further comprises a pair of stereo video cameras 500, which are placed between the two transmitting antenna arrays 201. The video cameras 500 create an additional monitoring angle (or view) 501 and allow for further measurements and calculations to be made on inspected objects, for example, they may be used as the method for measuring the thickness (t) of the object. The inspection procedure occurs as an individual carrying items 5 passes the monitored area between the two transmitting antenna arrays 201. Each signal transmits through any individual and carried or hidden items 5 as the individual and items move through the monitored area in either direction 40. As the target moves through the portal, the data from all receiving antennas/receivers 100 is transmitted to a processing unit (in some embodiments, the receiver itself contains a processing unit), which, in real time, makes a decision about the danger level of the target by comparing the calculated dielectric constants to a database of stored values, each of the value corresponding to specific known materials. The processing unit then sends an alarm signal to security officers if any such values correspond to dangerous materials, signaling that a risk exists. The processing unit may also be capable of sending a confirmation signal which would indicate that the object belongs to another preselected group of objects that may or may not be dangerous.

The present invention also comprises a system for detection of dangerous materials with units employing the steps of the method described above. Specifically, the system comprises a system for detecting an object belonging to one or more preselected groups of dangerous and non-dangerous objects in a monitored area, comprising: a transmitting antenna adapted to transmit an EM/MW signal through the monitored area and any object in said signal's path, a receiving antenna adapted to receive information regarding said signal after said signal transmits through the monitored area and any object in said signal's path, an instrument which can provide data on thickness of said object, and a processing unit adapted to determine an amplitude and a phase of said signal, determine whether said amplitude and phase meet a preset amplitude and phase threshold, determine a shift in an optical path length of said signal, determine the thickness of said object in the monitored area, determine a dielectric permittivity value of said object, and compare said dielectric permittivity value with a stored database of reference values to determine if a preselected object exists in the monitored area when the object's dielectric permittivity value matches that of one or more of the preselected groups of dangerous and non-dangerous objects.

In some aspects, the system comprises a processing unit adapted to determine a shift in an optical length of said signal by using a Fourier transformation modulus, relating and comparing the signal's complex amplitudes (i.e. amplitude and phase) in the presence of the object in the controlled/inspected/monitored area of space versus the signal's complex amplitudes in the absence of the object in the controlled area of space. In certain aspects, the system comprises a processing unit adapted to determine a dielectric permittivity value of the object which comprises equating the shift of optical path length to the value, $t^*(\sqrt{\in}-1)$, where t is the thickness of the object, and $\in$ is the dielectric permittivity value.

The field characteristics of a transmitting antenna used in the presently claimed method are tens to hundreds of times lower than the permitted threshold values determined by health standards, and thus are also harmless to the public's health.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A method for detecting and analyzing an object in a monitored area, comprising:
   emitting an electromagnetic/microwave (EM/MW) signal via at least one transmitter through the monitored area,
   transmitting said EM/MW signal through the monitored area, said signal transmitting through any object along a path directed towards at least one receiver located at a distance opposite of said one transmitter for receiving said signal,
   said receiver detecting an amplitude and a phase (complex amplitude) of a received EM/MW signal transmitted through the monitored area,
   said receiver further performing a first processing of said received signal to determine whether said amplitude is above, a preset amplitude threshold,
   said receiver further performing a second processing of said received signal if said preset amplitude threshold is met, said second processing comprising determining a shill in a length of an optical path of said EM/MW signal, compared to an optical path of the same signal through a free space, said shift occurring due to said EIVSMW signal transmitting through said object,
   wherein the shift in the length of the optical path is calculated by a Fourier transform of a relation between a signal's complex amplitudes in the presence of the object within the monitored area and the signal's complex amplitudes in the absence of the object within the monitored area,
   sending data regarding said shift to a processor,
   measuring a thickness (t) of said object and sending data regarding said thickness to said processor,
   said processor further calculating a dielectric permittivity value ($\in$) of said object via a relationship of said shift equating to ($t*(\sqrt{\in}-1)$),
   said processor comparing said dielectric permittivity value to a database of reference dielectric permittivity values forming preselected groups of objects, so as to determine to which preselected group of objects the object belongs and whether the object belongs to a preselected group of dangerous objects.

2. The method of claim 1, further comprising combining a plurality of EM/MW signals to form a real time distribution map of dielectric permittivity value data.

3. The method of claim 1, further comprising sending a confirmation or alarm signal in the presence of an object belonging to a particular preselected group of dangerous or non-dangerous objects.

4. The method of claim 3, wherein said signal is a silent signal.

5. The method of claim 1, further comprising one or more additional transmitters transmitting an EM/MW signal to said receiver.

6. The method of claim 1, further comprising one or more additional receivers receiving an EM/MW signal from said one transmitter.

7. The method of claim 1, wherein said one transmitter comprises an array of transmitting antennas.

8. The method of claim 1, wherein said one receiver comprises an array of receiving antennas.

9. The method of claim 1, further comprising one or more additional transmitters and one or more additional receivers, wherein each transmitter corresponds to only one receiver and each receiver corresponds to only one transmitter.

10. The method of claim 1, wherein said object is an irregularly shaped object.

11. The method of claim 1, wherein said object is detected in space and in time as it moves through the monitored area.

12. The method of claim 1, wherein said object is an optically transparent media.

13. The method of claim 1, wherein said object is an optically non-transparent media.

14. A system for detecting an object belonging to one or more preselected groups of dangerous and non-dangerous objects in a monitored area, comprising:
   a transmitting antenna adapted to transmit an EMSMW signal through the monitored area and any object in said signal's path,
   a receiving antenna adapted to receive information regarding said signal after said signal transmits through the monitored area and any object in said signal's path, an instrument which can provide data on thickness of said object,
   a processing unit adapted to determine an amplitude and a phase (complex amplitude) of said signal, determine whether said amplitude and phase meet a preset amplitude and phase threshold, determine a shift in an optical path length of said signal,
   wherein the processing unit is adapted to determine a shift in an optical length of said signal by a Fourier transformation modulus comparing a signal's amplitude and phase in the presence of the object within the monitored area and the signal's amplitude and area,
   determine the thickness of said object in the monitored area, determine a dielectric permittivity value of said object, and compare said dielectric permittivity value with a stored database of reference value to determine if a preselected object exists in the monitored area when the object's dielectric permittivity value matches that of one or more preselected groups of dangerous and non-dangerous objects, wherein the processing unit is adapted to determine a dielectric permittivity value of said object which comprises equating the shift of optical path length to $t*(\sqrt{\in}-1)$.

* * * * *